Figure 1:
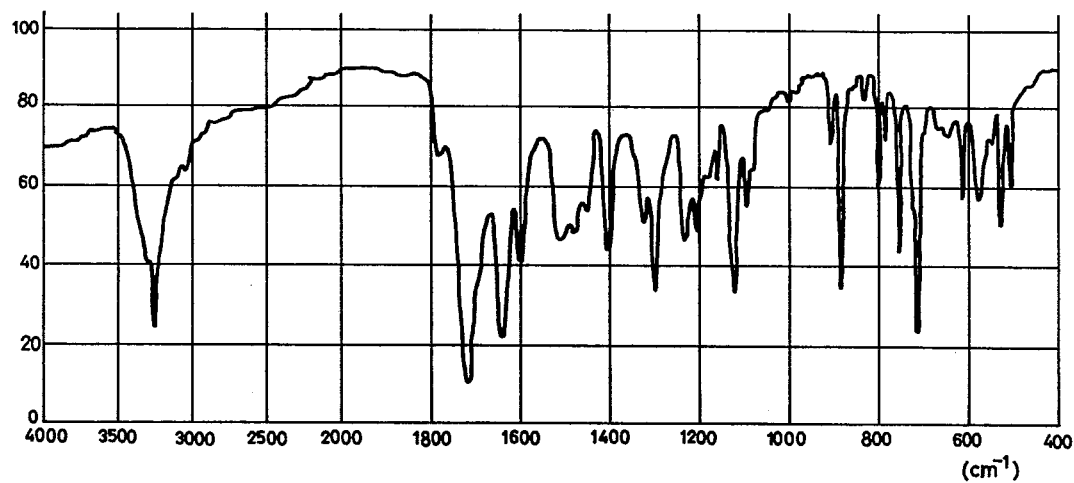

United States Patent [19]

Yoshikawa et al.

[11] 3,956,331

[45] May 11, 1976

[54] N-(SALICYLOYLAMINO)IMIDES AND PROCESS FOR THE PREPARATION OF THE SAME

[75] Inventors: Toshio Yoshikawa; Nagayoshi Sakamoto; Tomitada Nagamori, all of Ichihara, Japan

[73] Assignee: Ube Industries, Ltd., Yamaguchi, Japan

[22] Filed: Aug. 1, 1974

[21] Appl. No.: 493,514

[30] Foreign Application Priority Data

Feb. 26, 1974 Japan.............................. 49-21944

[52] U.S. Cl. ........................ 260/281 N; 260/45.8 R; 260/326 S; 260/326 C; 260/326 N
[51] Int. Cl.$^2$............... C07D 217/24; C07D 209/48
[58] Field of Search..................... 260/326 N, 281 N

[56] References Cited
UNITED STATES PATENTS 3,882,138    5/1975    Brouwer ......................... 260/326 N

OTHER PUBLICATIONS

Unishi et al., Chem. Abs. 69, 51871s.
Singh et al., J. Indian Chem. Soc. 45, 262 (1968).

*Primary Examiner*—Alton D. Rollins
*Assistant Examiner*—Mark L. Berch
*Attorney, Agent, or Firm*—Flynn & Frishauf

[57]    ABSTRACT

Novel N-(salicyloylamino)imides which can act as excellent stabilizers for polyolefins are disclosed. A process for the preparation of the same which comprises the reaction of salicyloylhydrazine with a cyclic acid anhydride is also disclosed.

9 Claims, 18 Drawing Figures

N-(SALICYLOYLAMINO)IMIDES AND PROCESS FOR THE PREPARATION OF THE SAME

This invention relates to a novel N-(salicyloylamino)imide and a process for the preparation of the same. More particularly, this invention is concerned with a novel N-(salicyloylamino)imide represented by the formula

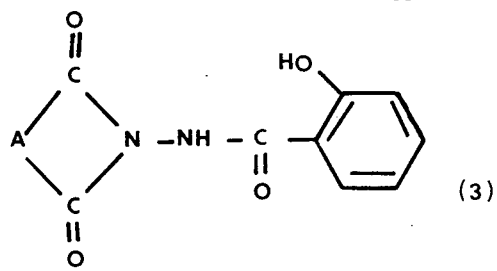

or

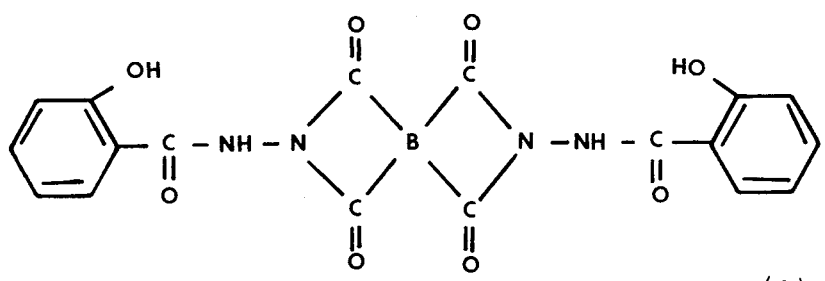

in which A represents a group

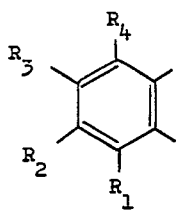

(in which $R^1$ - $R^4$ represent hydrogen atoms, halogen atoms, nitro groups, amino groups, carboxyl groups, hydroxyl groups, phenyl groups, phenylthio groups, or straight or branched alkyl, halogenated alkyl, alkoxyl, alkylthio, alkylamino or acylamino groups each having 1 to 5 carbon atoms),

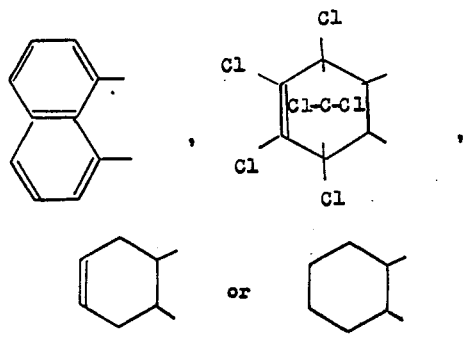

and B represents a group

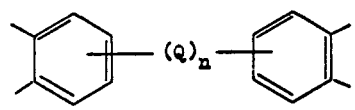

(in which Q represents an oxygen atom, a sulfur atom, a methylene group, a carbonyl group, a phenylene group, a phthaloyl group, an isophthaloyl group or a terephthaloyl group, and n is an integer of 0 or 1) or

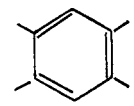

and a process for the preparation thereof which comprises the reaction of salicyloylhydrazine with a cyclic acid anhydride represented by the formula

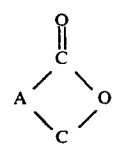

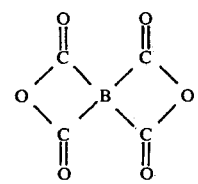

in which A and B are the same as above.

Therefore, an object of this invention is to provide a novel N-(salicyloylamino)imide which can act as an excellent stabilizer for polyolefins. Another object is to provide the N-(salicyloylamino)imide which can produce an excellent stabilizing effect against deteriorations caused by contact with heavy metals on polyolefins. A further object is to provide a process for the preparation of the N-(salicyloylamino)imide which comprises the reaction of salicyloylhydrazine with a certain cyclic acid anhydride. Other objects of this invention will be obvious from the contents of the specification hereinafter disclosed.

The cyclic acid anhydride represented by the aforementioned formula (1) is concretely exemplified by:

phthalic anhydride, 3-chlorophthalic anhydride, 4-chlorophthalic anhydride, 3,6-dichlorophthalic anhydride, 4,5-dichlorophthalic anhydride, tetrachlorophthalic anhydride, 3,6-dibromophthalic anhydride, tetrabromophthalic anhydride, 3-iodophthalic anhydride, 4-iodophthalic anhydride, 4,5-diiodophthalic anhydride, tetraiodophthalic anhydride, 3-fluorophthalic anhydride, 3,6-difluorophthalic anhydride, tetrafluorophthalic anhydride, 3-nitrophthalic anhydride, 4-nitrophthalic anhydride, 3-aminophthalic anhydride, 4-aminophthalic anhydride, trimellitic anhydride, 4-hydroxyphthalic anhydride, 3,6-dihydroxyphthalic anhydride, 3,6-dihydroxy-4-methylphthalic anhydride, 3-hydroxy-4-methoxyphthalic anhydride, 3-hydroxy-5-methoxyphthalic anhydride, 3-hydroxy-4,6-dimethylphthalic anhydride, 6-hydroxy-4-methoxy-3-methylphthalic anhydride, 3-(phenylthio)phthalic anhydride, 3-methyl-5-(phenylthio)phthalic anhydride, 3-methylphthalic anhydride, 4-methylphthalic anhydride, 3,4-dimethylphthalic anhydride, 3,6-dimethylphthalic anhydride, 4,5-dimethylphthalic anhydride, 3-propylphthalic anhydride, 6-isobutyl-3,4-dimethylphthalic anhydride, 3-methyl-6-(methylthio)phthalic anhydride, 5-(ethylthio)-3-methylphthalic anhydride, 3-(ethylthio)-6-methylphthalic anhydride, 3-ethyl-6-(ethylthio)phthalic anhydride, 4,6-dimethoxy-3-methylphthalic anhydride, 3-methoxy-4,6-dimethylphthalic anhydride, 4-isopropyl-3,5,6-trimethoxyphthalic anhydride, 3-(dibromomethyl)phthalic anhydride, 3-methoxyphthalic anhydride, 4-methoxyphthalic anhydride, 3,4-dimethoxyphthalic anhydride, 3,6-dimethoxyphthalic anhydride, 4,5-dimethoxyphthalic anhydride, 3,5-dimethoxy-4-methylphthalic anhydride, 3-(methylthio)phthalic anhydride, 3-(ethylthio)phthalic anhydride, 3-(propylthio)phthalic anhydride, 3-(dimethylamino)phthalic anhydride, 3-(isopropylamino)phthalic anhydride, 3-acetamidophthalic anhydride, 4-acetamidophthalic anhydride, 1,8-naphthalic anhydride, chlorendic anhydride (or 1,4,5,6,7,7-hexachloro-endo-5-norbornene-2,3-dicarboxylic anhydride), cis-4-cyclohexene-1,2-dicarboxylic anhydride and hexahydrophthalic anhydride (cyclohexane-1,2-dicarboxylic anhydride).

the cyclic acid anhydride represented by the aforementioned formula (2) is concretely exemplified by:

4,4'-di(phthalic anhydride) (or 3,4,3',4'-diphenyltetracarboxylic anhydride), 3,4'-di(phthalic anhydride), 4,4'-oxydi(phthalic anhydride), 3,3'-methylenedi(phthalic anhydride), 3,4'-methylenedi(phthalic anhydride), 4,4'-methylenedi(phthalic anhydride), 4,4'-carbonyldi(phthalic anhydride), 4,4'-(p-phenylene)di(phthalic anhydride), 4,4'-isophthaloyldi(phthalic anhydride), 4,4'-terephthaloyldi(phthalic anhydride) and pyromellitic anhydride.

The N-(salicyloylamino)imide represented by the aforementioned formulae (3) and (4) may be synthesized by reacting salicyloylhydrazine with a cyclic acid anhydride in the presence of a solvent. The solvent to be used in the reaction may preferably be a solvent capable of dissolving salicyloylhydrazine, a cyclic acid anhydride and N-(salicyloylamino)imide, and may be, for instance, N,N-dialkylacylamide such as N,N-dimethylformamide and N,N-dimethylacetamide or an aliphatic acid such as formic acid and acetic acid, but is not limited to these examples.

Salicyloylhydrazine and a cyclic acid anhydride may preferably be in the ratio of equivalent molar amounts in the synthesis of N-(salicyloylamino)imide represented by the formula (3), and in the molar ratio of 2 : 1 (former : latter) in the synthesis of N-(salicyloylamino)imide represented by the formula (4). However, the present reaction may proceed in the absence of these conditions.

The reaction temperature and the reaction period may vary depending on the kinds of cyclic acid anhydrides, solvents and the like. Any temperature below a boiling point of the solvent used may be adopted, and, in general, a temperature in the range of 20° to 120°C may be adopted. The reaction period may generally be between 10 minutes and 15 hours.

The resulting N-(salicyloylamino)imides can easily be recovered, after completion of the reaction, by removing the solvent under reduced pressure from the reaction mixture and by washing the residue with an alcohol such as methanol and ethanol or by cooling the reaction mixture to room temperature, pouring this into a large amount of water and collecting the obtained solid by filtration.

The N-(salicyloylamino)imides reprsented by the aforementioned formula (3) are concretely exemplified by:

N-(salicyloylamino)phthalimide, 3-chloro-N-(salicyloylamino)phthalimide, 4-chloro-N-(salicyloylamino)phthalimide, 3,6-dichloro-N-(salicyloylamino)phthalimide, 4,5-dichloro-N-(salicyloylamino)phthalimide, 3,4,5,6-tetrachloro-N-(salicyloylamino)phthalimide, 3,6-dibromo-N-(salicyloylamino)phthalimide, 3,4,5,6-tetrabromo-N-(salicyloylamino)phthalimide, 3-iodo-N-(salicyloylamino)phthalimide, 4-iodo-N-(salicyloylamino)phthalimide, 4,5-diiodo-N-(salicyloylamino)phthalimide, 3,4,5,6-tetraiodo-N-(salicyloylamino)phthalimide, 3-fluoro-N-(salicyloylamino)phthalimide, 3,6-difluoro-N-(salicyloylamino)phthalimide, 3,4,5,6-tetrafluoro-N-(salicyloylamino)phthalimide, 3-nitro-N-(salicyloylamino)phthalimide, 4-nitro-N-(salicyloylamino)phthalimide, 3-amino-N-(salicyloylamino)phthalimide, 4-amino-N-(salicyloylamino)phthalimide, 4-carboxy-N-(salicyloylamino)phthalimide, 4-hydroxy-N-(salicyloylamino)phthalimide, 3,6-dihydroxy-N-(salicyloylamino)phthalimide, 3,6-dihydroxy-4-methyl-N-(salicyloylamino)phthalimide, 3-hydroxy-4-methoxy-N-(salicyloylamino)phthalimide, 3-hydroxy-5-methoxy-N-(salicyloylamino)phthalimide, 3-hydroxy-4,6-dimethyl-N-(salicyloylamino)phthalimide, 6-hydroxy-4-methoxy-3-methyl-N-(salicyloylamino)phthalimide, 3-(phenylthio)-N-(salicyloylamino)phthalimide, 3-methyl-5-(phenylthio)-N-(salicyloylamino)phthalimide, 3-methyl-N-(salicyloylamino)phthalimide, 4-methyl-N-(salicyloylamino)phthalimide, 3,4-dimethyl-N-(salicyloylamino)phthalimide, 3,6-dimethyl-N-(salicyloylamino)phthalimide, 4,5-dimethyl-N-(salicyloylamino)phthalimide, 3-propyl-N-(salicyloylamino)phthalimide, 6-isobutyl-3,4-dimethyl-N-(salicyloylamino)phthalimide, 3-methyl-6-(methylthio)-N-(salicyloylamino)phthalimide, 5-(ethylthio)-3-methyl-N-(salicyloylamino)phthalimide, 3-(ethylthio)-6-methyl-N-(salicyloylamino)phthalimide, 3-ethyl-6-(ethylthio)-N-(salicyloylamino)phthalimide, 4,6-dimethoxy-3-methyl-N-(salicyloylamino)phthalimide, 3-methoxy-4,6-dimethyl-N-(salicyloylamino)phthalimide, 4-isopropyl-3,5,6-trimethoxy-N-(salicyloylamino)phthalimide, 3-(dibromomethyl)-N-(salicyloylamino)phthalimide, 3-methoxy-N-(salicyloylamino)phthalimide, 4-methoxy-N-(salicyloylamino)phthalimide, 3,4-dimethoxy-N-

(salicyloylamino)phthalimide, 3,6-dimethoxy-N-(salicyloylamino)phthalimide, 4,5-dimethoxy-N-(salicyloylamino)phthalimide, 3,5-dimethoxy-4-methyl-N-(salicyloylamino)phthalimide, 3-(methylthio)-N-(salicyloylamino)phthalimide, 3-(ethylthio)-N-(salicyloylamino)phthalimide, 3-(propylthio)-N-(salicyloylamino)phthalimide, 3-acetamido-N-(salicyloylamino)phthalimide, 4-acetamido-N-(salicyloylamino)phthalimide, 3-(dimethylamino)-N-(salicyloylamino)phthalimide, 3-(isopropylamino)-N-(salicyloylamino)phthalimide, N-(salicyloylamino)-1,8-naphthalimide, N-(salicyloylamino)chlorendic imide, N-(salicyloylamino)-cis-4-cyclohexene-1,2-dicarboxylimide and N-(salicyloylamino)-cyclohexane-1,2-dicarboxylimide.

The N-(salicyloylamino)imides represented by the aforementioned formula (4) are concretely exemplified by:
4,4'-bis[N-(salicyloylamino)phthalimide], 3,4'-bis[N-(salicyloylamino)phthalimide], 4,4'-oxybis[N-(salicyloylamino)phthalimide], 3,3'-methylenebis[N-(salicyloylamino)phthalimide], 4,4'-methylenebis[N-(salicyloylamino)phthalimide], 4,4'-carbonylbis[N-(salicyloylamino)phthalimide], 4,4'-(p-phenylene)-bis[N-(salicyloylamino)phthalimide],4,4'-isophthaloylbis[N-(salicyloylamino)phthalimide], 4,4'-terephthaloylbis[N-(salicyloylamino)phthalimide] and N,N'-bis(salicyloylamino)-1,2,4,5-benzenetetracarboxyl-1,2,4,5-diimide.

N-(salicyloylamino)acid imides prepared by the process of the present invention are novel compounds, and are useful as stabilizers for polyolefines such as polyethylene, polypropylene and the like due to their excellent stabilizing effects against deterioration caused by contact with, especially, heavy metals. (See reference examples)

The process of the present invention will be illustrated by the following examples. Salicyloylhydrazines employed in these examples were prepared by the following steps:

25 weight parts of methyl salicylate and 20 weight parts of hydrazine hydrate (85 %) were heated under reflux for 4 hours in the presence of 100 weight parts of ethanol; after removal of the ethanol under reduced pressure, the residue was cooled; the precipitate thus obtained was collected by filtration and washed with distilled water; and the resulting residue was recrystallized from ethanol to yield the desired compound, m.p. 147°C.

SYNTHESIS OF N-(SALICYLOYLAMINO)PHTHALIMIDE

Example 1

Figure 2:
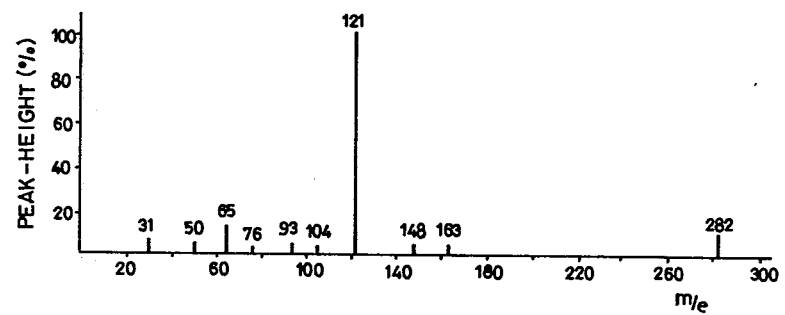

In a flask equipped with a stirrer and a thermometer were placed 2.96 g of phthalic anhydride, 3.04 g of salicyloylhydrazine and 50 ml of N,N-dimethylformamide. The reaction was carried out with stirring for 3.5 hours at a temperature kept at 83°C. After completion of the reaction, the reaction mixture was cooled to room temperature and poured into 2 liters of water to precipitate a white solid. The solid was collected by filtration, washed with ethanol and dried under reduced pressure to yield 4.1 g of a white powder, m.p. 252° – 253°C. The powder thus obtained was easily soluble in acetone at room temperature, hardly soluble in ethanol at room temperature, soluble in acetic acid, benzene and chloroform in hot states, and insoluble in ethyl ether, petroleum ether, n-hexane and carbon tetrachloride in hot states. This powder was indentified as N-(salicyloylamino)phthalimide by the elemental analysis, IR spectrum (KBr tablet, the same hereinafter) (FIG. 1) and Mass spectrum (FIG. 2).

Found (%): C, 63.93; H, 3.55; N, 10.04. Calcd. for $C_{15}H_{10}N_2O_4$ (%): C, 63.82; H, 3.55; N, 9.93.

Examples 2 to 6

The same reactions as in Example 1 except that the amounts of phthalic anhydride and salicyloylhydrazine, the kind and amount of the solvent, the reaction temperature and the reaction period all set forth in Table 1 were employed were carried out. After completion of the reaction, the treatments were performed in the same manner as in Example 1 except that the resultants were poured into water in the amount shown in Table 1 to give white powders in the yields shown in Table 1. All of the melting points, solubilities in the solvents, IR spectra and Mass spectra were precisely identical with those of N-(salicyloylamino)phthalimide obtained in Example 1.

Example 7

In a flask equipped with a reflux apparatus were placed 2.96 g of phthalic anhydride, 3.04 g of salicyloylhydrazine and 50 ml of N,N-dimethylformamide, and the reaction was performed under reflux for 3 hours. After removing the N,N-dimethylformamide from the reaction mixture under reduced pressure (2 – 3 mmHg, abs.), the residue was washed with ethanol to yield 4.3 g of a white powder, which had the same characteristics as N-(salicyloylamino)phthalimide obtained in Example 1.

Table 1

| Example | Amount of phthalic anhydride (g) | Amount of salicyloylhydrazine (g) | Kind and amount of solvent (ml) | Reaction temperature (°C) | Reaction period (hr) | Amount of water (l) | Yield (g) |
| --- | --- | --- | --- | --- | --- | --- | --- |
| 2 | 4.30 | 3.04 | N,N-dimethylformamide 50 | 100 | 3.5 | 2 | 4.7 |
| 3 | 29.6 | 30.4 | do. 100 | 90 | do. | 6 | 50 |
| 4 | 2.96 | 3.04 | do. 20 | 35 | 12 | 2 | 3.8 |
| 5 | 5.92 | 6.08 | do. 150 | 50 | 10 | do. | 6 |
| 6 | 2.96 | 3.04 | N,N-dimethylacetamide 40 | 100 | 3 | do. | 3.9 |

SYNTHESIS OF N-(SALICYLOYLAMINO)-CYCLOHEXANE-1,2-DICARBOXYLIMIDE

Example 8

Figure 3:
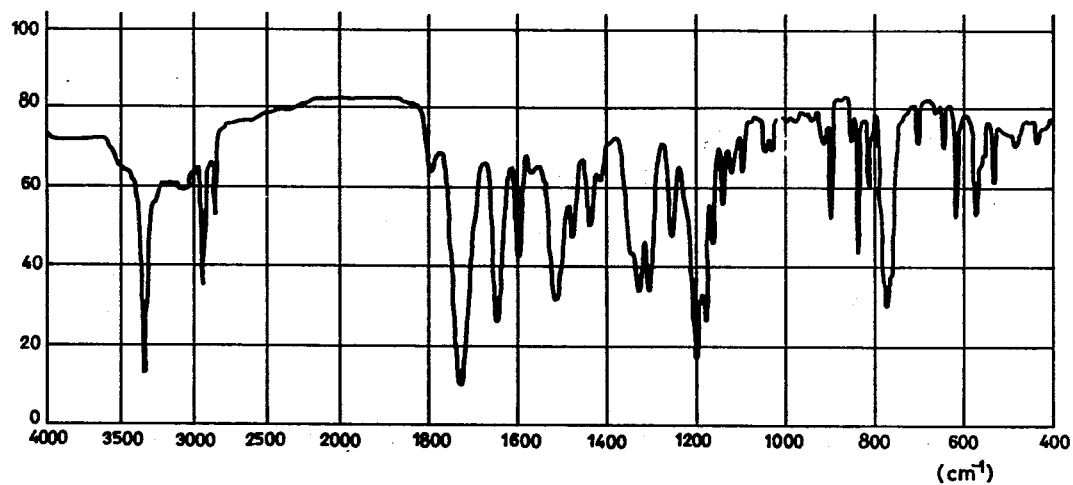
Figure 4:
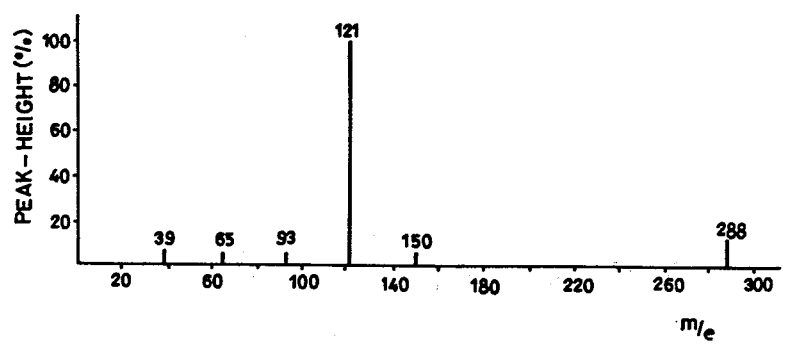

In a flask equipped with a stirrer and a thermometer were placed 3.04 g of hexahydrophthalic anhydride, 3.04 g of salicyloylhydrazine and 20 ml of N,N-dimethylformamide, and the reaction was performed with stirring for 3.5 hours at a temperature kept at 84°–85°C. After completion of the reaction, the reaction mixture was treated in the same manner as in Example 1 to give 5.2 g of a white powder, m.p. 227°C. The obtained powder was soluble in acetone at room temperature and hardly soluble in ethanol, acetic acid, benzene, chloroform, carbon tetrachloride and petroleum ether at room temperature. This powder was identified as N-(salicyloylamino)-cyclohexane-1,2-dicarboxylimide by the elemental analysis, IR spectrum (FIG. 3) and Mass spectrum (FIG. 4).

Found (%): C, 62.27; H, 5.65; N, 9.67. Calcd. for $C_{15}H_{16}N_2O_4$ (%): C, 62.50; H, 5.56; N, 9.72.

Example 9

The same reaction as in Example 7 except that 3.08 g of hexahydrophthalic anhydride, 3.04 g of salicyloylhydrazine and 50 ml. of N,N-dimethylformamide were used was carried out. Further the treatment was then performed in the same manner as in Example 7 to give 4.7 g of a white powder. The powder thus obtained was precisely identical with N-(salicyloylamino)-cyclohexane-1,2-dicarboxylimide obtained in Example 8 in solubilities in the solvents, a melting point, IR spectrum and Mass spectrum.

Example 10

The same reaction as in Example 1 except that 4.12 g of hexahydrophthalic anhydride, 3.04 g of salicyloylhydrazine and 30 ml of N,N-dimethylformamide were used and 40°C of the reaction temperature and 10 hours of the reaction period were employed was carried out. After completion of the reaction, the reaction mixture was then treated in the same manner as in Example 1 to give 5 g of a white powder. The powder thus obtained was precisely identical with N-(salicyloylamino)-cyclohexane-1,2-dicarboxylimide obtained in Example 8 in solubilities in the solvents, a melting point, IR spectrum and Mass spectrum.

Example 11

The same reaction as in Example 1 except that 3.08 g of hexahydrophthalic anhydride, 3.04 g of salicyloylhydrazine and 30 ml of N,N-dimethylacetamide were used was carried out. The reaction mixture was then treated in the same manner as in Example 1 to give 4.5 g of a white powder, which had the same characteristics as N-(salicyloylamino)-cyclohexane-1,2-dicarboxylimide obtained in Example 8.

SYNTHESIS OF N-(SALICYLOYLAMINO)-CIS-4-CYCLOHEXENE-1,2-DICARBOXYLIMIDE

Example 12

Figure 5:
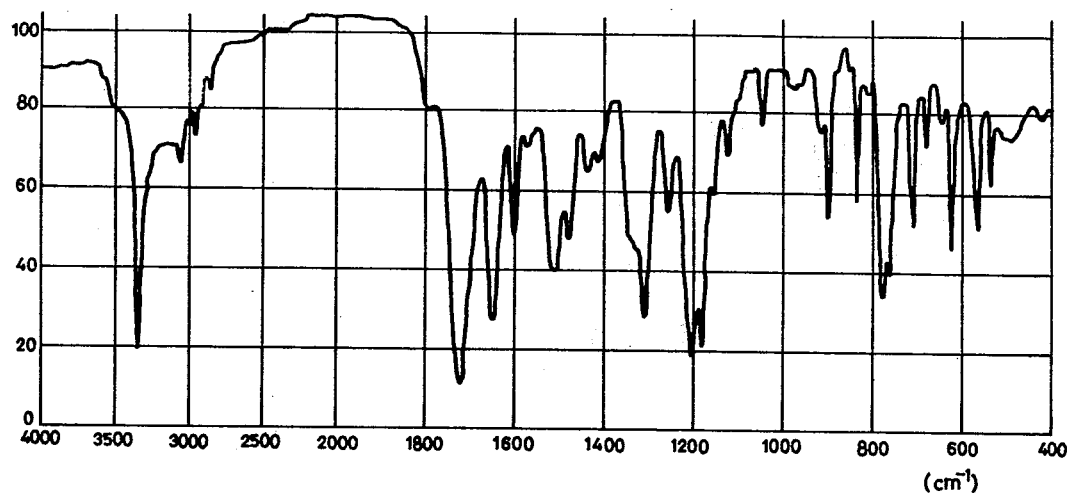
Figure 6:
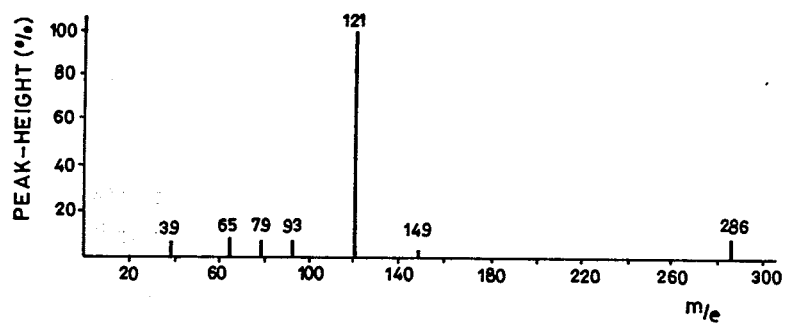

The same reaction as in Example 1 except that 3.04 g of cis-4-cyclohexene-1,2-dicarboxylic anhydride, 3.04 g of salicyloylhydrazine and 20 ml of N,N-dimethylformamide were used and 89°C of the reaction temperature and 3 hours of the reaction period were employed was carried out. The reaction mixture was then treated in the same manner as in Example 1 to give 3 g of a white powder, m.p. 192°–192.5°C. The powder thus obtained was soluble in acetone, ethanol, acetic acid, chloroform and benzene at room temperature and insoluble in petroleum ether, ligroin, n-hexane and carbon tetrachloride in hot states. Further, the powder was identified as N-(salicyloylamino)-cis-4-cyclohexene-1,2-dicarboxylimide by the elemental analysis, IR spectrum (FIG. 5) and Mass spectrum (FIG. 6).

found (%): C, 62.18; H, 4.77; N, 9.79. Calcd. for $C_{15}H_{14}N_2O_4$ (%): c, 62.94; H, 4.90; N, 9.70.

Example 13

The same reaction as in Example 7 except that 6.08 g of cis-4-cyclohexane-1,2-dicarboxylic anhydride, 3.04 g of salicyloylhydrazine and 50 ml of N,N-dimethylformamide were used was carried out. The reaction mixture was then treated in the same manner as in Example 7 to give 4.8 g of a white powder. The powder thus obtained was precisely identical with N-(salicyloylamino)-cis-4-cyclohexane-1,2-dicarboxylimide obtained in Example 12 in a melting point, solubilities in the solvents, IR spectrum and Mass spectrum.

Example 14

The same reaction as in Example 1 except that 40 g of cis-4-cyclohexene-1,2-dicarboxylic anhydride, 40 g of salicyloylhydrazine and 150 ml of N,N-dimethylformamide were used and 120°C of the reaction temperature and 4 hours of the reaction period were employed was carried out. The reaction mixture was then treated in the same manner as in Example 1 to give 63 g of a white powder, which had the same characteristics as N-(salicyloylamino)-cis-4-cyclohexene-1,2-dicarboxylimide obtained in Example 12.

Example 15

The same reaction as in Example 1 except that 3.04 g of cis-4-cyclohexene-1,2-dicarboxylic anhydride, 3.04 g of salicyloylhydrazine and 20 ml of N,N-dimethylacetamide were used and 80°C of the reaction temperature and 3 hours of the reaction period were empolyed was carried out. The reaction mixture was then treated in the same manner as in Example 1 to give 2.5 g of a white powder, which had the same characteristics as N-(salicyloylamino)-cis-4-cyclohexene-1,2-dicarboxylimide obtained in Example 12.

SYNTHESIS OF 3,4,5,6-TETRACHLORO-N-(SALICYLOYLAMINO)-PHTHALIMIDE

Example 16

Figure 7:
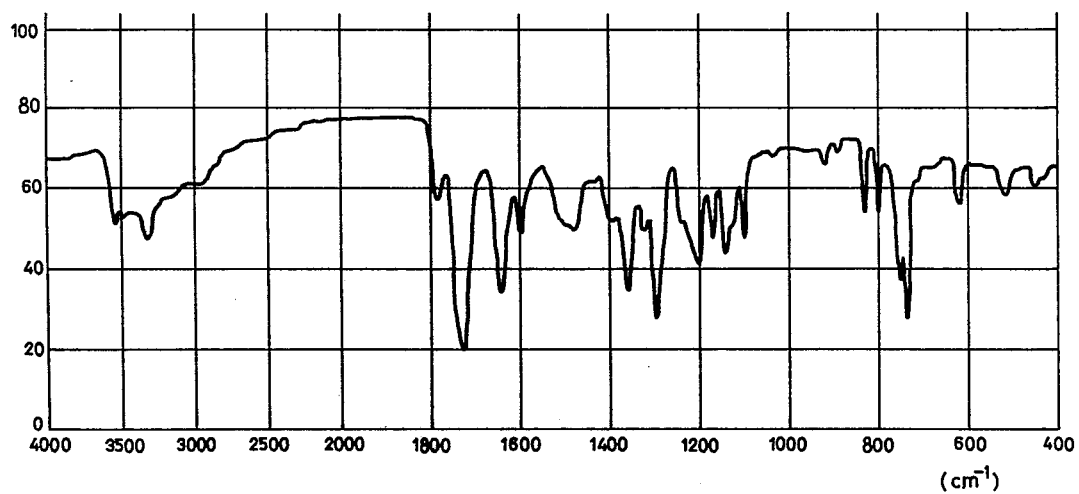
Figure 8:
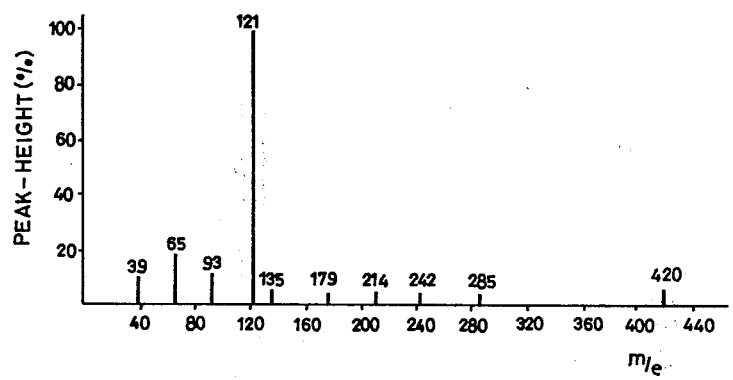

The same reaction as in Example 1 except that 2.86 g of tetrachlorophthalic anhydride, 1.52 g of salicyloylhydrazine and 10 ml of N,N-dimethylformamide were used and 85°C of the reaction temperature and 3 hours and 45 minutes of the reaction period were employed was carried out. The reaction mixture was then treated in the same manner as in Example 1 to give 3.5 g of yellow crystals, m.p. 290°–293°C. The crystals thus obtained were soluble in acetone at room temperature, soluble in acetic acid, chloroform and ethanol in hot states and hardly soluble in benzene and carbon tetrachloride. Further, the crystals were identified as 3,4,5,6-tetrachloro-N-(salicyloylamino)phthalimide by the elemental analysis, IR spectrum (FIG. 7) and Mass spectrum (FIG. 8).

Found (%): C, 42.86; H, 1.60; N, 6.56; Cl, 32.62. Calcd. for $C_{15}H_6N_2Cl_4O_4$ (%): C, 42.86; H, 1.43; N, 6.67; Cl, 33.81.

SYNTHESIS OF N-(SALICYLOYLAMINO)-4-CARBOXYPHTHALIMIDE

Example 17

Figure 9:
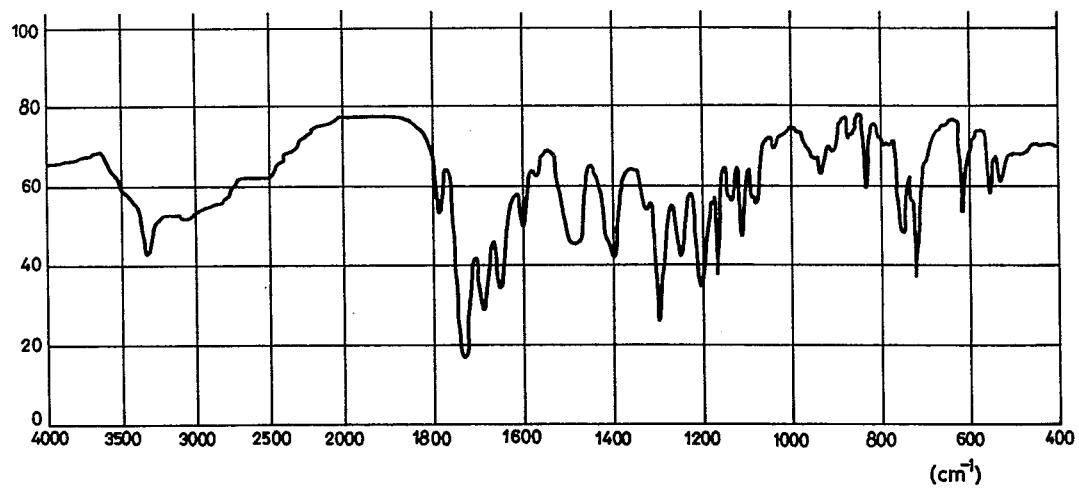
Figure 10:
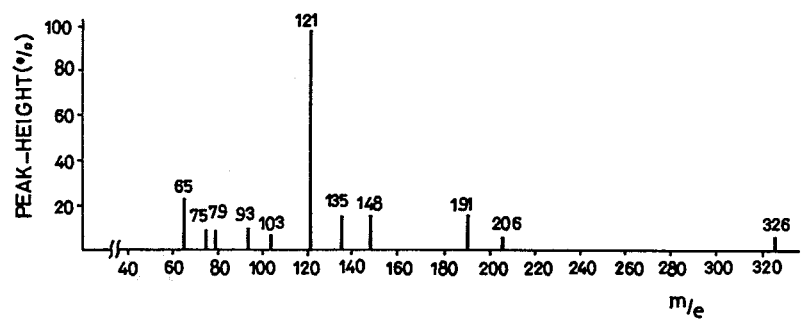

The same reaction as in Example 1 except that 1.92 g of trimellitic anhydride, 1.52 g of salicyloylhydrazine and 10 ml of N,N-dimethylformamide were used was carried out. The reaction mixture was then treated in the same manner as in Example 1 to give 2.1 g of a white powder, m.p. 288.5°–290°C. The powder thus obtained was soluble in ethanol, acetic acid and acetone in hot states, and insoluble in chloroform and carbon tetrachloride. The powder was identified as N-(salicyloylamino)-4-carboxyphthalimide by the elemental analysis, IR spectrum (FIG. 9) and Mass spectrum (FIG. 10).

Found (%): C, 58.33; H, 3.06; N, 8.65. Calcd. for $C_{16}H_{10}N_2O_6$ (%): C, 58.90; H, 3.07; N, 8.59.

SYNTHESIS OF N-(SALICYLOYLAMINO)-1,8-NAPHTHALIMIDE

Example 18

Figure 11:
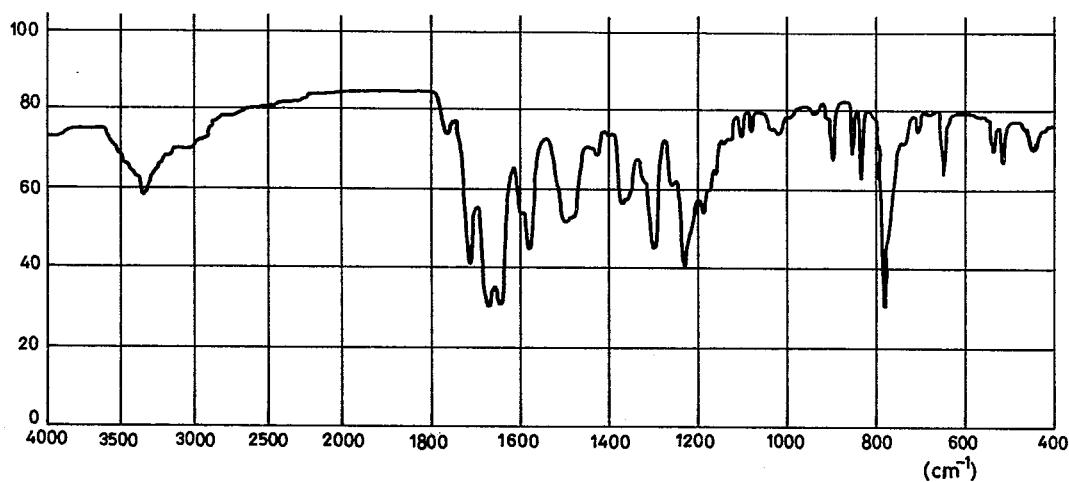
Figure 12:
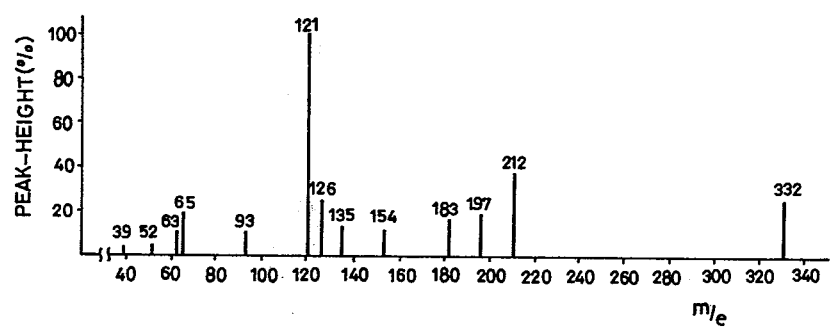

The same reaction as in Example 1 except that 1.98 g of 1,8-naphthalic anhydride, 1.52 g of salicyloylhydrazine and 20 ml of N,N-dimethylformamide were used and 81°–83°C of the reaction temperature was employed was carried out. The reaction mixture was then treated in the same manner as in Example 1 to give 3 g of a yellow powder, m.p. 268°C. The powder thus obtained was soluble in benzene at room temperature, soluble in chloroform, acetic acid and ethanol in hot states and insoluble in n-hexane and ethyl ether. Further, the powder was identified as N-(salicyloylamino)-1,8-naphthalimide by the elemental analysis, IR spectrum (FIG. 11) and Mass spectrum (FIG. 12).

Found (%): C, 68.02; H, 3.57; N, 8.05. Calcd. for $C_{19}H_{12}N_2O_4$ (%): C, 68.67; H, 3.61; N, 8.43.

SYNTHESIS OF N-(SALICYLOYLAMINO)-CHLORENDIC IMIDE

Example 19

Figure 13:
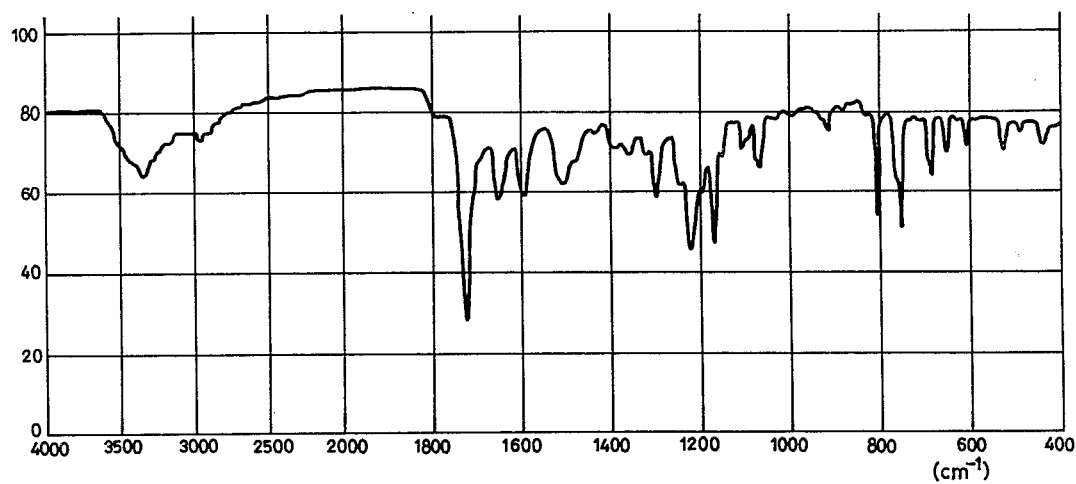
Figure 14:
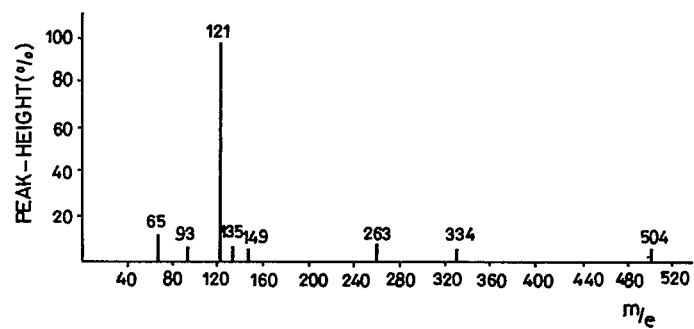

The same reaction as in Example 1 except that 3.71 g of chlorendic anhydride, 1.52 g of salicyloylhydrazine and 10 ml of N,N-dimethylformamide were used was carried out. The reaction mixture was then heated in the same manner as in Example 1 to give 1.5 g of an earth brown powder, m.p. 317°C. The powder thus obtained was soluble in chloroform, ethanol and acetone at room temperature, soluble in hot acetic acid and insoluble in benzene, carbon tetrachloride and ethyl ether. Further, the powder was identified as N-(salicyloylamino)-chlorendic imide by the elemental analysis, IR spectrum (FIG. 13) and Mass spectrum (FIG. 14).

Found (%): C, 37.80; H, 1.68; N, 5.42; Cl, 42.33. Calcd. for $C_{16}H_8N_2O_4Cl_6$ (%): C, 38.02; H, 1.58; N, 5.54; Cl, 42.18.

SYNTHESIS OF N,N'-BIS(SALICYLOYLAMINO)-1,2,4,5-BENZENETETRACARBOXYL-1,2,4,5-DIIMIDE

Example 20

Figure 15:
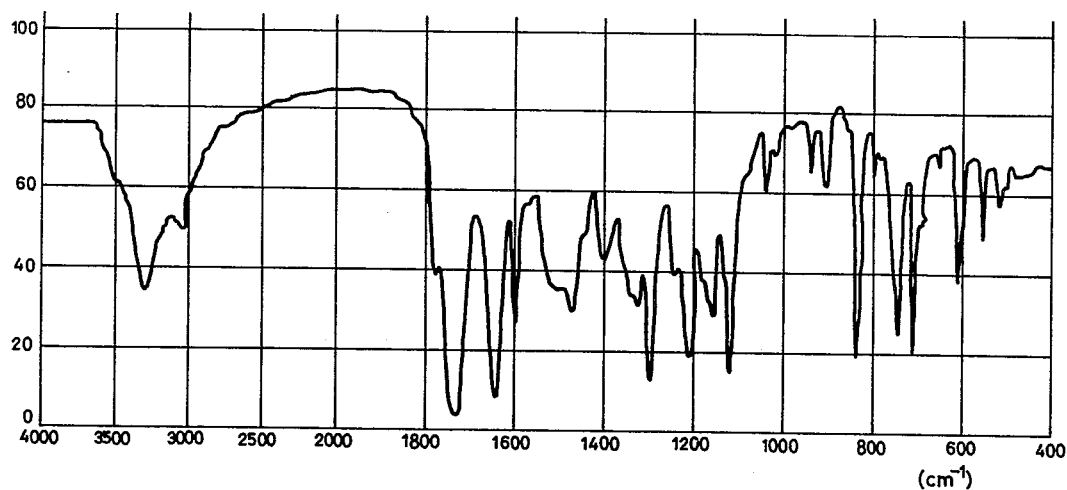
Figure 16:
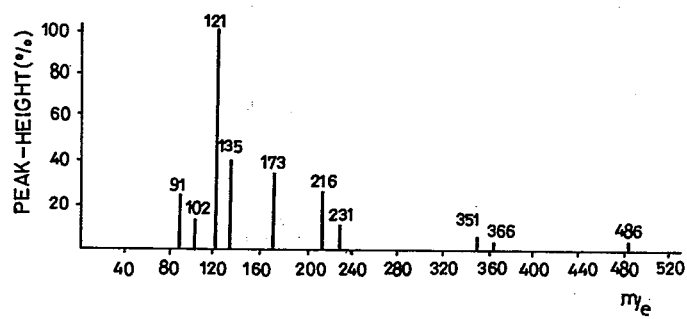

The same reaction as in Example 1 except that 2.0 g of pyromellitic anhydride, 3.0 g of salicyloylhydrazine and 50 ml of N,N-dimethylformamide were used was carried out. The reaction mixture was then treated in the same manner as in Example 1 to give 1.7 g of a white powder, m.p. 365°–366°C. The powder thus obtained was hardly soluble in even ethanol, benzene, acetone, ethyl ether, carbon tetrachloride and chloroform in hot states. Further, the powder was identified as N,N'-bis(salicyloylamino)-1,2,4,5-benzenetetracarboxyl-1,2,4,5-diimide by the elemental analysis, IR spectrum (FIG. 15) and Mass spectrum (FIG. 16).

Found (%): C, 59.20; H, 2.83; N, 11.68. Calcd. for $C_{24}H_{14}N_4O_8$ (%): C, 59.26; H, 2.88; N, 11.52.

Example 21

The same reaction as in Example 7 except that 10.9 g of pyromellitic anhydride, 15.2 g of salicyloylhydrazine and 100 ml of N,N-dimethylformamide were used and the reflux period of 5 hours was employed was carried out. The reaction mixture was then treated in the same manner as in Example 7 to give 18 g of a white powder. The powder thus obtained was precisely identical with N,N'-bis(salicyloylamino)-1,2,4,5-benzenetetracarboxyl-1,2,4,5-diimide obtained in Example 20 in a melting point, solubilities in the solvents, elemental analysis, IR spectrum and Mass spectrum.

SYNTHESIS OF 4,4'-BIS[N-(SALICYLOYLAMINO)PHTHALIMIDE]

Example 22

Figure 17:
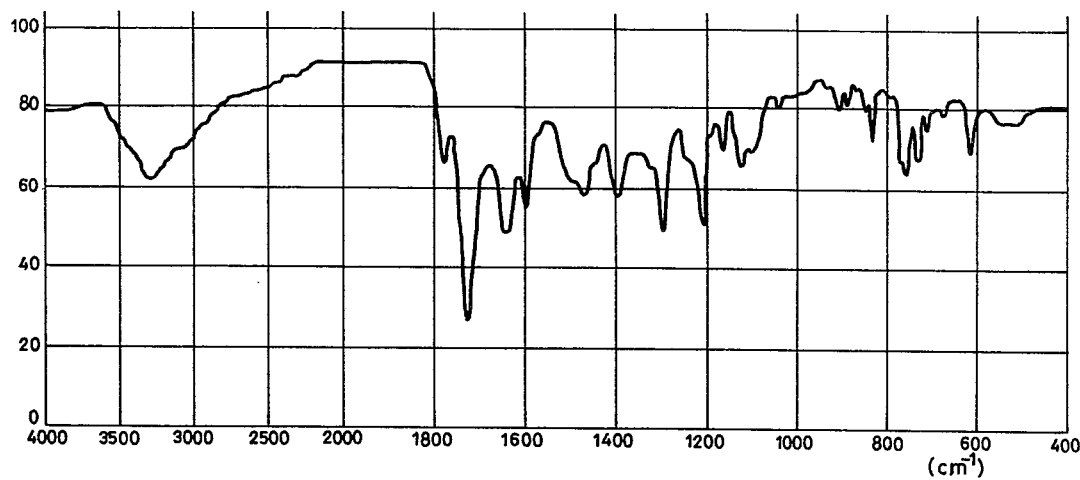

The same reaction as in Example 1 except that 2.94 g of 4,4'-di(phthalic anhydride), 3.10 g of salicyloylhydrazine and 10 ml of N,N-dimethylformamide were used and 80°C of the reaction temperature and 5 hours of the reaction period were employed was carried out. The reaction mixture was then treated in the same manner as in Example 1 to give 3.2 g of a white powder, m.p. 345°–347°C. The powder thus obtained was identified as 4,4'-bis[N-(salicyloylamino)phthalimide] by the elemental analysis and IR spectrum (FIG. 17).

Found (%): C, 64.44; H, 3.44; N, 9.84. Calcd. for $C_{30}H_{18}N_4O_8$ (%): C, 64.06; H, 3.20; N, 9.96.

SYNTHESIS OF 3,4'-BIS[N-(SALICYLOYLAMINO)PHTHALIMIDE]

Example 23

Figure 18:
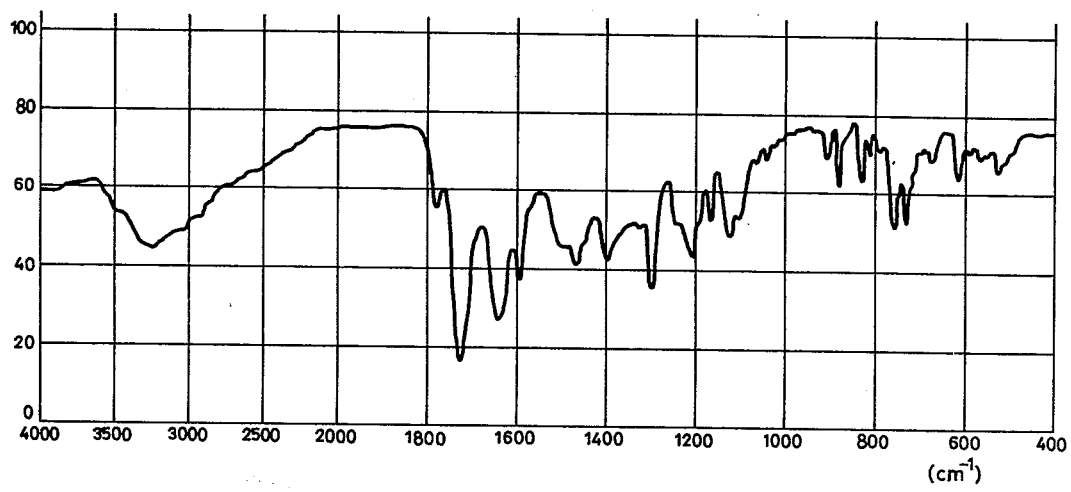

The same reaction as in Example 1 except that 2.94 g of 3,4'-di(phthalic anhydride), 3.10 g of salicyloylhydrazine and 10 ml of N,N-dimethylformamide were used and 90°C of the reaction temperature and 7 hours of the reaction period were employed was carried out. The reaction mixture was then treated in the same manner as in Example 1 to give 4.5 g of a white powder, m.p. 217°C. The powder was soluble in acetone at room temperature, soluble in acetic acid and ethanol in hot states and insoluble in even benzene and chloroform in hot states. The powder thus obtained was identified as 3,4′-bis-[N-(salicyloylamino)phthalimide] by the elemental analysis and IR spectrum (FIG. 18).

Found (%): C, 64.63; H, 3.76; N, 10.55. Calcd. for $C_{30}H_{18}N_4O_8$ (%): C, 64.06; H, 3.20; N, 9.96.

The following reference examples show the stabilizing effects of N-(salicyloylamino)imides obtained according to the process of the present invention on polyolefins. In addition, the stabilizing effects of publicity known stabilizers are also shown in following comparative reference examples. The term "part" means "weight part" and "M.I." means "Melt Flow Index" which was determined in accordance with ASTMD 1238. The notations shown in reference examples mean the following stabilizers.

A: N-(salicyloylamino)phthalimide
B: N-(salicyloylamino)-cyclohexane-1,2-dicarboxylimide
C: N-(salicyloylamino)-cis-4-cyclohexene-1,2-dicarboxylimide
D: 3,4,5,6-tetrachloro-N-(salicyloylamino)phthalimide
E: N-(salicyloylamino)-4-carboxylphthalimide
F: N-(salicyloylamino)-1,8-naphthalimide
G: N-(salicyloylamino)-chlorendic imide
H: N,N′-bis(salicyloylamino)-1,2,4,5-benzenetetracarboxyl-1,2,4,5-diimide
I: 4,4′-bis[N-(salicyloylamino)phthalimide]
J: 3,4′-bis[N-(salicyloylamino)phthalimide]
a: oxamide
b: oxanilide
c: oxalobis(benzylidenehydrazide)
d: N-salicylidene-N′-salicyloylydrazide
e: tetrakis-[methylene 3-(3,5-di-tert-butyl-4-hydroxyphenyl)propionate]methane
f: 4,4′-thiobis(3-methyl-6-tert-butylphenol)
g: dioctadecyl-3,3′-thiodipropionic acid ester
h: trilauryltrithiophosphite REFERENCE EXAMPLES 1 to 10

1. Preparation of test piece

Into Brabender plastograph (available from Brabender Corporation, West Germany) adjusted to 60 r.p.m. of rotation speed and a temperature of 140°C were charged 100 parts of ethylene homopolymer with no additives (M.I. = 0.2) which had been prepared by a high pressure process. Two minutes later, 0.10 part of an antioxidant, tetrakis[methylene 3-(3,5-di-tert-butyl-4-hydroxyphenyl)-propionate]methane, and 0.15 part of a stabilizer set forth in Table 2 were added thereto. Another 2 minutes later, 0.10 part of copper stearate was added to the mixture, which was subsequently kneaded for 8 minutes. The mixture was then heated on a plate of 190°C for 1 minute and pressed at a pressure of 300 kg/cm² for 1 minute by means of a spacer to form a film having a thickness of 0.25 mm. A round film of 4 mm in its diameter was prepared by punching of the obtained film, and employed as a test piece.

2. Determination of anti-deteriorating effect

The period required for appearance of a peak showing generation of heat caused by oxidation was determined by means of Standard-Type Rapidly Fluctuating Differential Calorimeter (available from Rigaku Denki Kogyo Ltd., Japan). The calorimeter received a test piece in one sample dish and the other disk remained empty. After the atmosphere of the calorimeter was replaced with oxygen, the environmental temperature was elevated to 195°C in an instant (about 5 – 10 seconds) by means of inside heating system with flow of oxygen into the system at a rate of 180 ml/min. Subsequently, the temperature was elevated to 200°C for a period of about 30 seconds, and kept at 200°C. The period from the time when the temperature reached 200°C to the time when there appeared a peak showing generation of heat caused by oxidation of the test piece (minutes: induction period) was measured and adopted to estimate an anti-deteriorating effect.

The results obtained according to the above-mentioned process are shown in Table 2.

Table 2

| Reference example | Stabilizer | Induction period (min.) |
|---|---|---|
| 1 | A | 59 |
| 2 | B | 65 |
| 3 | C | 58 |
| 4 | D | 48 |
| 5 | E | 29 |
| 6 | F | 52 |
| 7 | G | 42 |
| 8 | H | 33 |
| 9 | I | 35 |
| 10 | J | 30 |

COMPARATIVE REFERENCE EXAMPLES 1 TO 6

Test pieces were prepared by the method described in Reference example 1 except using no stabilizer and no copper stearate, using no stabilizer only or using publicly known stabilizers in the amount set forth in Table 3 in place of the stabilizer obtained by the process of the present invention. Their effects were determined in the manner described in Reference example 1 and their results are shown in Table 3.

Table 3

| Comparative ref. example | Kind and amount (part) of stabilizer | | Amount of copper stearate (part) | Induction period (min.) |
|---|---|---|---|---|
| 1 | — | — | — | 39.0 |
| 2 | — | — | 0.10 | 0 |
| 3 | a | 0.15 | do. | 17.4 |
| 4 | b | do. | do. | 20.5 |
| 5 | c | do. | do. | 25..8 |
| 6 | d | do. | do. | 27.3 |

REFERENCE EXAMPLES 11 TO 20

1. Preparation of test piece

Into the same Brabender plastograph as employed in Reference example 1 which was adjusted to 60 r.p.m. of rotation speed and a temperature of 200°C were charged 100 parts of isotactic polypropylene with no additives (M.I. = 5). Two minutes later, 0.03 part of e, 0.10 part of g and 0.20 part of h, all of which were publicly known stabilizers and, in addition, 0.5 part of a stabilizer obtained by the process of the present invention which is set forth in Table 4 were added thereto. Another 2 minutes later, 1.5 parts of copper powder was added to the mixture, which was subsequently kneaded for 8 minutes. The mixture was then heated on a plate of 200°C for 1 minute and pressed at a pressure of 300 kg/cm² for 1 minute by means of a spacer to form a film having a thickness of 1.0 mm. The film thus obtained was employed as a test piece.

b. Determination of anti-deteriorating effect

The test piece was kept in Geer's oven (inside temperature: 150°C), and a period (in hours) until the test piece turned yellow and deteriorated was measured and adopted as "Heat stable duration".

The results thus obtained are shown in Table 4.

Table 4

| Ref. example | Stabilizer | Heat stable duration (hr) |
|---|---|---|
| 11 | A | 145 |
| 12 | B | 160 |
| 13 | C | 140 |
| 14 | D | 135 |
| 15 | E | 65 |
| 16 | F | 140 |
| 17 | G | 130 |
| 18 | H | 105 |
| 19 | I | 120 |
| 20 | J | 85 |

COMPARATIVE REFERENCE EXAMPLE 7

A test piece was prepared in the same manner as in Reference example 11 except that the publicly known stabilizer *d* was employed in the amount of 0.5 part in place of the stabilizer A obtained by the process of this invention. The test piece thus obtained was measured in its effect in the same manner as in Reference example 11 to show 40 hours of the heat stable duration.

REFERENCE EXAMPLES 21 TO 25

Into the Brabender plastograph adjusted to 60 r.p.m. of rotation speed and a temperature of 200°C were charged 100 parts of isotactic polypropylene with no additives (M.I. = 5). Two minutes later, 0.2 part of a stabilizer set forth in Table 5 was added thereto, and the mixture was subsequently kneaded for 8 minutes. The mixture was then heated on a plate of 190°C and pressed at a pressure of 100 kg/cm² to form a polypropylene sheet having a thickness of 0.5 mm.

five of the test pieces thus obtained were placed in Fade-meter (xenon arc, inside temperature: 65°C) to expose to radiation, withdrawn therefrom, and bent. The radiation period, at the end of which there appeared a crack in the test piece when the piece was bent, was measured and adopted as "Light stable duration." The longest and shortest periods among the periods measured on these five pieces were adopted. The results are shown in Table 5.

Table 5

| Ref. example | Stabilizer | Light stable duration (hr) |
|---|---|---|
| 21 | A | 300 – 360 |
| 22 | B | 320 – 370 |
| 23 | C | 315 – 360 |
| 24 | H | 350 – 420 |
| 25 | I | 340 – 400 |

COMPARATIVE REFERENCE EXAMPLE 8

The same measurement as in Reference example 21 except for employing no stabilizer was repeated to shown 35 – 55 hours of the light stable duration.

What is claimed is:

1. N-(salicyloylamino)imide represented by the formula

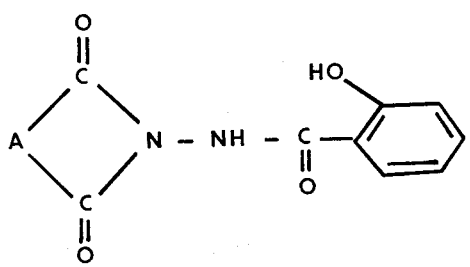

in which A represents a group

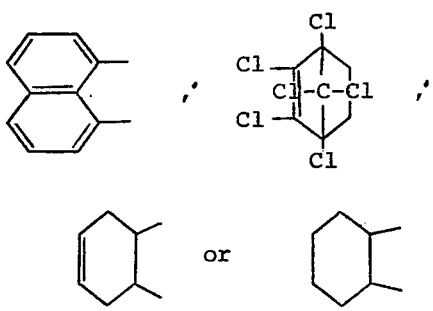

in which $R_1$–$R_4$ represent hydrogen atoms, halogen atoms, hydroxyl groups, straight chain alkyl groups having from 1 to 5 carbon atoms, alkoxyl groups having from 1 to 5 carbon atoms, or alkylthio groups having from 1 to 5 carbon atoms, and one of $R_1$ – $R_4$ can be replaced with a nitro group, a carboxyl group or a branched chain alkyl group having from 1 to 5 carbon atoms;

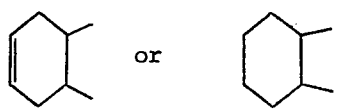

2. An N-(salicyloylamino)imide of claim 1, in which A represents a group

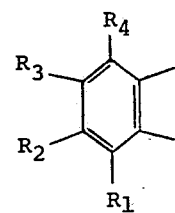

in which $R_1$–$R_4$ represent hydrogen atoms, halogen atoms, hydroxyl groups, straight chain alkyl groups having from 1 to 5 carbon atoms, alkoxy groups having from 1 to 5 carbon atoms, or alkylthio groups having from 1 to 5 carbon atoms.

3. An N-(salicyloylamino)imide of claim 1, in which A represents

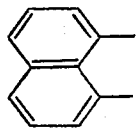

4. An N-(salicyloylamino)imide of claim 1, in which A represents

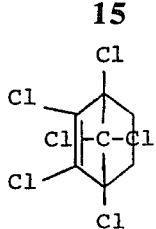

5. An N-(salicyloylamino)imide of claim 1, in which A represents

6. An N-(salicyloylamino)imide of claim 1, in which A represents

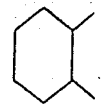

7. An N-(salicyloylamino)imide of claim 1, in which all of $R_1$–$R_4$ represent hydrogen atoms.

8. An N-(salicyloylamino)imide of claim 1, in which all of $R_1$–$R_4$ represent chlorine atoms.

9. An N-(salicyloylamino)imide of claim 1, in which one of $R_1$–$R_4$ represents a carboxyl group and the others represent hydrogen atoms.

* * * * *

UNITED STATES PATENT OFFICE
CERTIFICATE OF CORRECTION

PATENT NO. : 3,956,331
DATED : May 11, 1976
INVENTOR(S) : TOSHIO YOSHIKAWA et al

It is certified that error appears in the above-identified patent and that said Letters Patent are hereby corrected as shown below:

Column 3, line 41:

replace "the" with --- The ---.

Column 14, line 56, Claim 2:

replace "alkoxy" with --- alkoxyl ---.

UNITED STATES PATENT OFFICE
CERTIFICATE OF CORRECTION

PATENT NO. : 3,956,331  
DATED : May 11, 1976  
INVENTOR(S) : TOSHIO YOSHIKAWA et al

It is certified that error appears in the above-identified patent and that said Letters Patent are hereby corrected as shown below:

Column 14, line 35, second formula (Claim 1) and

Column 15, line 5 (Claim 4):

delete the formula and replace with:

--- 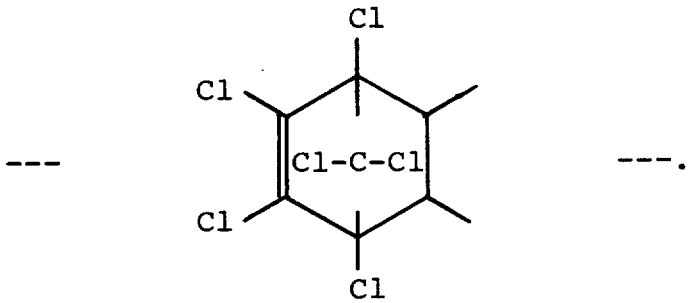 ---.

Signed and Sealed this

Thirtieth Day of November 1976

[SEAL]

Attest:

RUTH C. MASON  
*Attesting Officer*

C. MARSHALL DANN  
*Commissioner of Patents and Trademarks*